United States Patent [19]

Drauz et al.

[11] Patent Number: 4,533,766

[45] Date of Patent: Aug. 6, 1985

[54] PROCESS FOR THE PRODUCTION OF DIHYDROXYBENZENES

[75] Inventors: Karlheinz Drauz, Freigericht; Axel Kleemann, Hanau, both of Fed. Rep. of Germany

[73] Assignee: Degussa Aktiengesellschaft, Frankfurt, Fed. Rep. of Germany

[21] Appl. No.: 587,654

[22] Filed: Mar. 8, 1984

[30] Foreign Application Priority Data

Mar. 11, 1983 [DE] Fed. Rep. of Germany ....... 3308769

[51] Int. Cl.$^3$ .............................................. C07C 37/00
[52] U.S. Cl. .................................... 568/771; 568/629; 568/733; 568/741; 568/768
[58] Field of Search ............... 568/768, 629, 771, 741, 568/733

[56] References Cited

U.S. PATENT DOCUMENTS

| | | | |
|---|---|---|---|
| 2,900,412 | 8/1959 | Toland | 568/800 |
| 3,943,179 | 3/1976 | Bost et al. | 568/771 |
| 4,053,523 | 10/1977 | Seifert et al. | 568/771 |
| 4,111,967 | 9/1978 | Martin et al. | 568/771 |
| 4,258,219 | 3/1981 | Kato et al. | 568/771 |

Primary Examiner—Werren B. Lone
Attorney, Agent, or Firm—Cushman, Darby & Cushman

[57] ABSTRACT

The known nuclear hydroxylation of substituted phenols or phenol ethers with organic solutions of hydrogen peroxide in the presence of a catalyst is carried out in improved manner by employing both (1) a special, practically water free solution of hydrogen peroxide in an organic solvent which forms an azeotrope with water, which azeotrope boils below the boiling point of hydrogen peroxide, and (2) sulfur dioxide as a catalyst. Through this, the nuclear hydroxylation is substantially simpler than previously; difficult separations, e.g., from water-phenol, or the separation and recovery of the catalyst are eliminated. Besides, the yields are increased.

30 Claims, No Drawings

PROCESS FOR THE PRODUCTION OF DIHYDROXYBENZENES

BACKGROUND OF THE INVENTION

The invention is directed to the production of dihydroxybenzenes as well as their monoethers by nuclear hydroxylation of the corresponding monophenol or phenol ether with hydrogen peroxide.

Important dihydroxybenzenes are derivatives of phenol, the naphthols, and also derivatives of anthracene and phenanthrene. They are employed in the production of dyestuffs, in the production of synthetic resins, in photography, and for the production of important plant protectives.

Their production, therefore, has long been the object of thorough investigations. The hydroxylation has been carried out both with hydrogen peroxide itself as well as with hydroperoxides, peroxides, or even per acids such as, e.g., performic acid or peracetic acid.

Nevertheless, hydrogen peroxide was preferred since it is the most readily available and since with percarboxylic acids, hydroperoxides and peroxides side reactions occur (European published application No. 0027593).

There was always present a catalyst in these hydroxylations. This catalyst can be a metalloid such as sulfur, selenium, tellurium, phosphorus, arsenic, or antimony in elemental form (German OS No. 2348957) or there can be used boron compounds (German Pat. No. 1543830). Various processes operate with transition elements in the form of their ions (German OS No. 2162552), especially with iron ions (German OS No. 2162589 or German Pat. No. 2407398) or cobalt ions (German AS No. 2341743), or even with the corresponding oxides (Milas U.S. Pat. No. 2,395,638).

Besides, there are employed strong acids such as sulfuric acid, sulfonic acids (German OS No. 2138735, German AS No. 2410742, German AS No. 2410758, German AS No. 2462967), or a mixture of sulfuric acid and phosphoric acid (German OS No. 2138735), there are also mentioned in the last named published application organic acids such as, inter alia, trichloroacetic acid or tartaric acid.

The already mentioned percarboxylic acids likewise serve as catalysts (French Pat. No. 1479354). In all of the mentioned catalysts, it is a matter with the catalysts being solid or liquid materials. Hydrogen peroxide, as preferred oxidation agent, for the most part is employed in aqueous solutions of various concentrations up to very high concentrations which have the danger of explosion; thus, the process according to German Pat. No. 2064497 operates with solutions which only contain 5 weight % water, but even at this highly concentrated hydrogen peroxide the yield of dihydroxy derivatives was only 70% and was reduced considerably according to the dilution of the hydrogen peroxide.

Additionally, in these and also in other processes, the operation must be carried out with a very large excess of the phenol to be hydroxylated in order in general to obtain the above-stated yield. If this excess is reduced, e.g., from 20 moles to 10 moles per mole of hydrogen peroxide, then the yield is reduced drastically despite the higher concentration of hydrogen peroxide.

However, as is known, this type of excess of a reactant, which must be recycled, requires additional industrial expense; above all in regard to the size of the apparatus employed.

Since care is always taken to avoid large excesses of one component as far as possible, there have been attempts to avoid employing aqueous solutions of hydrogen peroxide.

Thus, different solutions of hydrogen peroxide in organic solvents have already been used. For example, according to the process of German Pat. No. 2410758, there are preferably employed hydrogen peroxide solutions in derivatives of phosphoric acid or phosphonic acid, namely in the presence of a strong acid, such as sulfuric acid (100%) or fluorosulfonic acid.

However, these highly concentrated strong acids have the disadvantage that their separation from the reaction mixture creates difficulties (German AS No. 2658943), above all since their concentration in the reaction mixture has a considerable influence on the length of the reaction.

The excess of phenol was indeed reduced somewhat in contrast to this in the process of German AS No. 2064497, but this did not outweigh the disadvantage of the strong acids.

An additional difficulty in the process of German Pat. No. 2410758 in the working up of the reaction mixture was produced by the presence of the water formed after the reaction with hydrogen peroxide.

Since the solvent for hydrogen peroxide employed in part is higher boiling than the phenols employed and these frequently, above all phenol itself, form an azeotrope with water whose boiling point is below that of the organic solvent, it was highly problematic that a trouble-free separation of the phenols from the reaction mixture could be attained.

Therefore, other ways were tried, first to manage without catalyst, i.e., above all without the strong acids. Since the catalysts above all were needed for the activation of hydrogen peroxide, the process of German AS No. 2658943 was operated with organic solutions of peracetic acid. An additional catalyst was not used.

Entirely apart from the fact that the mentioned process presupposes a complete plant for the production of an organic percarboxylic acid, which first is obtained from hydrogen peroxide and carboxylic acid, and thereupon is produced by extraction of this so-called "equilibrium acid" from its aqueous solution, it has been shown a stated good selectivity and good yield was only possible in the presence of additional peracid stabilizers (German OS No. 2364181; European OS No. 0027593). Also, the attempt to produce pyrocatechol and hydroquinone without catalyst with gaseous hydrogen peroxide could be carried out only poorly on an industrial scale because of the danger of explosion (Japan published application No. 24056/1974).

From what has been said above, the result is that processes in which hydrogen peroxide is used as the most readily accessible hydroxylating agent do not make possible any entirely satisfactory process for the industrial production of dihydroxybenzenes.

Therefore, in recent times, there have only been developed processes which do not directly use hydrogen peroxide and in part for this reason require high industrial expense.

The subject matter of the invention, therefore, is carrying out the nuclear hydroxylation of substituted phenols or their ethers with hydrogen peroxide in the presence of catalysts in an industrially simple manner and with very good yields.

SUMMARY OF THE INVENTION

It has now been found that this problem can be solved by employing an organic solution of hydrogen peroxide if the reaction is carried out in the presence of sulfur dioxide and with a water-free solution of hydrogen peroxide, which preferably has a water content below 0.5 weight %, e.g., 0.1%, and which is produced with an organic solvent which forms an azeotrope with water, which azeotrope has a boiling point below the boiling point of hydrogen peroxide, referred to normal pressure. As "water free" there is intended solutions which at most have up to 1 weight % of water.

As solvents, there can be used ethers such as dioxane, diisopropyl ether, methyl tert. butyl ether.

Preferred solvents are alkyl or cycloalkyl esters of saturated aliphatic carboxylic acids which contain 4–8 carbon atoms, e.g., alkyl alkanoates.

Especially suitable esters are those of acetic acid and propionic acid, above all n-propyl acetate or isopropyl acetate.

Other suitable esters include ethyl acetate, hexyl acetate, butyl acetate, sec. butyl acetate, amyl acetate, cyclohexyl acetate, cyclopentyl acetate, methyl propionate, ethyl propionate, propyl propionate, isopropyl propionate, butyl propionate, methyl butyrate, ethyl butyrate, n-propyl butyrate, ethyl valerate, ethyl hexanoate.

There can also be used mixtures of esters.

The organic hydrogen peroxide solutions can be stabilized in customary manner, see Ullmann, Enzyklopadie der technischen Chemie, 4th Edition, Vol. 17, page 709, the entire disclosure of which is hereby incorporated by reference and relied upon.

The mentioned solutions of hydrogen peroxide in alkyl or cycloalkyl esters are obtained according to the process of German OS No. 3225307.9, the entire disclosure of which is hereby incorporated by reference and relied upon.

The sulfur dioxide acting as catalyst can be used in the gaseous form. Sulfur dioxide, however, can also be dissolved in a solvent at pleasure, which does not enter into a disturbing reaction with sulfur dioxide or with hydrogen peroxide, for example in dialkyl ethers, e.g., dipropyl ether, diisopropyl ether or dibutyl ether, esters of phosphoric acid or phosphonic acid, e.g., trioctyl phosphate, tributyl phosphate, diethyl phthalate, diethyl methane phosphonate, dibutyl ethane phosphonate, etc. The concentration depends on the solubility of $SO_2$ in the solvent. Generally, it is between 0.1 and 50, preferably 1 to 10 weight %. However, it is favorable to employ sulfur dioxide as a solution in one of the above described carboxylic acid esters. Sulfur dioxide is used in very small amounts, i.e., in amount of 0.0001 to 0.1 mole, preferably from 0.0005 to 0.01 mole based on 1 mole of hydrogen peroxide, above all compared with hydroxylations catalyzed by protonic acids on the acid side.

The reaction generally occurs at 20° to 200° C., preferably at a temperature of 40° to 180° C.

The organic solution of hydrogen peroxide in the mentioned alkyl or cycloalkyl esters makes possible higher concentrations (up to 60 weight %).

As stated above, the process of the invention is directed to carrying out the nuclear hydroxylation of substituted phenols as well as of phenol monoethers. Thus, there can be hydroxylated alkyl derivatives of phenol, e.g., 2-chlorophenol, 3-chlorophenol, 4-chlorophenol, 2-fluorophenol, 3-fluorophenol, 4-fluorophenol, 4-carbomethoxyphenol, 2-methylphenol, 3-methylphenol, 4-methylphenol, 4-cyclohexylphenol, 2-cyclohexylphenol, 4-phenylphenol, 3-phenylphenol, 2-phenylphenol, 4-ethylphenol, 3-ethylphenol, 2-ethylphenol, 2-isopropylphenol, 3-isopropylphenol, 4-isopropylphenol, 4-tert.-butylphenol, phenylmethylether, 4-chlorophenylmethylether, 3-chlorophenylmethylether, 2-chlorophenylmethylether, 4'-methylphenylmethylether, 3'-methylphenylmethylether, 4-methoxy-1-phenylbenzene, ethyl-phenylether, isoproylphenylether, isoproyl-4-methylphenylether, 1-hydroxynaphthalene, 2-hydroxynaphthalene, 1-methoxynaphthalene, 1-hydroxy-2-methylnaphthalene, 1-hydroxy-4-methylnaphthalene, 2-hydroxy-1-methylnaphthalene, 2-hydroxy-6-methylnaphthalene, 1-hydroxy-4-isopropylnaphthalene, 1-hydroxy-4-tert.-butyl-naphthalene, 1-hydroxy-6-phenylnaphthaline, 1-hydroxy-6-methoxynaphthaline, isopropyl-1-naphthylether, isopropyl-2-naphthylether, phenyl-1-naphthylether, phenyl-2-naphthylether, 1-hydroxyanthracene, 1-methoxyanthracene, 2-hydroxyanthracene, 2-methoxyanthracene, 1-hydroxyphenanthrene, 3-hydroxyphenanthrene, 9-methoxyphenanthrene, 3-methoxyphenanthrene, 1-methoxyphenanthrene.

There can also be used halogen substituted phenols or alkoxy substituted phenols, e.g., 4-chlorophenol, 4-bromophenol, 4-fluorophenol, 3-chlorophenol, 2,4-dichlorophenol, 2-methoxyphenol, 4-ethoxyphenol.

The pressure is not critical for the reaction. Generally, the reaction is carried out at normal pressure.

The duration of the reaction depends on the temperature and the concentration of the sulfur dioxide.

In order to establish the best reaction time, there can be carried out a small-scale experiment.

Preferably, the procedure is such that after 30 minutes more than 95% of the hydrogen peroxide employed is reacted.

The hydroxylation of the substituted phenols or phenol ethers according to the process of the invention is especially successful if water-free solutions of hydrogen peroxide in the mentioned carboxylic acid esters are employed with a weight ratio of about 1:4 to 2:1 $H_2O_2$/carboxylic acid ester.

This weight ratio is also attained in using less concentrated $H_2O_2$ solutions by distilling off overhead from these solutions the carboxylic acid ester which is mixed with the phenol derivative. The removal of the ester can be controlled by any desired value.

The distillation is carried out in such manner that practically no phenol and no hydrogen peroxide is carried out with the carboxylic acid ester.

As a positive side effect, there takes place an azeotropic removal of water from the phenol since the azeotrope water/carboxylic acid ester is the lowest boiling component.

The preparation of the reaction mixture is substantially simpler than the methods previously known.

Since the ester used as solvent according to the invention boils lower than the phenols which are converted, first there is distilled off an azeotrope between the ester and the water. The difficulties of a water-phenol separation, such as previously occurred, are eliminated. This is especially important since the phenols are used in excess and must be returned again.

In the preparation, it is not absolutely necessaary, because of the extremely low catalyst concentrations, to carry out a separation of the catalyst, for example, by neutralization, before a distillative separation. The crude reaction mixture is subjected directly to a distillation.

The molar ratio of phenol and hydrogen peroxide is between 5 to 20:1, preferably 5 to 15:1, very favorably at 10:1.

In the process of the invention, it is true that a catalyst is employed. However, it is used in such a slight amount that a special separation of it before the distillative working up of the reaction mixture is superfluous as mentioned above.

Additionally, there is produced a very favorable space-time-yield because of the short reaction times. Thus, for the industrial carrying out of the operation, small reaction volumes are sufficient. Thus, there are present 99% or more conversion after only 20 to 30 minutes.

Besides through the short duration of the reaction, there is simultaneously reduced the possible danger of decompositions. This reaction also can be readily carried out continuously.

Furthermore, it is substantial that the volatile solvent together with the water present can be separated from the residual phenol and the reaction products without trouble so that the phenol can be returned into the reaction step again in practically water-free condition.

All of these advantages are not tied to a reduction of the yields obtained according to the previous state of the art, but instead the yields are even increased.

It has proven especially favorable to use freshly produced solutions of sulfur dioxide.

Unless otherwise indicted, all parts and percentages are by weight.

The process can comprise, consist essentially of, or consist of the stated steps with the recited materials.

The invention is explained in more detail in connection with the following examples.

DETAILED DESCRIPTION

Example 1

150.2 grams (1.0 mole) of 4-tert. butyl phenol were heated to 100° C. There were added to the stirred melt 0.4 gram of a 4.8 weight % solution of sulfur dioxide in n-propyl acetate and subsequently 6.37 grams of a 53.4 weight % water-free solution of hydrogen peroxide in n-propyl acetate (0.1 mole). The temperature in the reaction solution increased after that to 155° C. After the exotherm died down, there was determined after 20 minutes a hydrogen peroxide reaction of 99.4%. The reaction mixture then contained 13.4 grams of 4-tert. butyl pyrocatechol, which corresponds to a yield of 81.1% based on the hydrogen peroxide reacted.

Example 2

108.1 grams (1.0 mole) of p-cresol were heated. There were added to the stirred melt 0.4 grams of a 4.8 weight % solution of sulfur dioxide in n-propyl acetate and subsequently 11.15 grams of a 30.5 weight % water-free solution of hydrogen peroxide in n-propyl acetate (0.1 mole). The temperature in the reaction solution increased after that to 149° C. After the exotherm died down, there was determined after 15 minutes a hydrogen peroxide reaction of 99.8%. The reaction mixture then contained 8.84 grams (71.2 mmoles) of 4-methyl pyrocatechol, which corresponds to a yield of dihydroxybenzenes of 80.3%, based on the hydrogen peroxide reacted.

Example 3

170.2 grams (1.0 mole) of 4-hydroxybiphenyl in 300 ml of n-propyl acetate were heated to 80° C. There were added to the strongly stirred reaction mixture 0.6 gram of a 14.8 weight % solution of sulfur dioxide in n-propyl acetate and subsequently 6.37 grams of a 53.4 weight % water-free solution of hydrogen peroxide in n-propyl acetate (0.1 mole $H_2O_2$). The temperature in the reaction mixture increased after that to 128° C. After the exotherm died down, after 30 minutes there was established a hydrogen peroxide reaction of 98.7%. The reaction mixture then contained 10.2 grams (59.9 mmoles) of 1,2-dihydroxy-4-phenylbenzene, which corresponds to a yield of 60.7%, based on the hydrogen peroxide reacted.

Example 4

108.1 grams (1.0 mole) of anisole were heated to 80° C. There were added to the stirred melt 0.4 gram of a 4.8 weight % solution of sulfur dioxide in n-propyl acetate and subsequently 6.37 grams of a 53.4 weight % water-free solution of hydrogen peroxide (0.1 mole) in ethyl acetate. The temperature in the reaction mixture increased to 140° C. After 30 minutes there was determined a hydrogen peroxide reaction of 97.9%. The reaction mixture then contained 5.28 grams (42.5 mmoles) of the monomethyl ether of pyrocatechol and 2.36 grams (19.0 mmoles) of hydroquinone monomethyl ether, which corresponds to a total yield of 63.1% based on the hydrogen peroxide reacted.

Example 5

122.2 grams (1.0 mole) of 4-ethyl phenol were heated to 70° C. There were added to the stirred melt 0.4 gram of a 4.8 weight % solution of sulfur dioxide in n-propyl acetate and subsequently 11.15 grams of 30.5 weight % water-free solution of hydrogen peroxide (0.1 mole) in n-propyl acetate. The temperature in the reaction mixture increased to 150° C. After the exotherm died down, there was established after 15 minutes a hydrogen peroxide reaction of 99.5%. The reaction mixture then contained 7.24 grams (52.4 mmoles) of 4-ethyl pyrocatechol and 1.79 grams (12.95 mmoles) of 4-ethyl resorcinol, which corresponds to a yield of dihydroxybenzenes of 65.6% based on the hydrogen peroxide employed.

Example 6

108.1 grams (1.0 mole) of o-cresol were heated to 90° C. There were added to the stirred melt 0.4 gram of a 4.8 weight % solution of sulfur dioxide in n-propyl acetate and subsequently 11.15 grams of a 30.5 weight % water-free solution of hydrogen peroxide in n-propyl acetate (0.1 mole). The temperature increased to 146° C. After the exotherm died down, there was ascertained after 20 minutes a hydrogen peroxide reaction of 99.6%. The reaction mixture then contained 6.0 grams (48.3 mmoles) of 3-methyl pyrocatechol and 2.95 grams (23.8 mmoles) of 2-methyl-hydroquinone, which corresponds to a yield of 72.4% based on the hydrogen peroxide reacted.

The entire disclosure of German priority application P.3308769.5 is hereby incorporated by reference.

What is claimed is:

1. A process for the production of a substituted dihydroxybenzene, a hydroxy alkoxy benzene, a substituted hydroxy alkoxy benzene, a dihydroxy anthracene, a dihydroxy naphthalene, a dihydroxy alkyl naphthalene, 1. a hydroxynaphthyl ether, a hydroxyphenanthryl ether, a hydroxyanthracenyl ether or a dihydroxy phenanthrene by nuclear hydroxylation of phenol with hydrogen peroxide in a substantially water-free organic solvent in the presence of a catalyst comprising reacting an alkyl phenol, an aryl phenol, a halophenol, an alkoxyphenol, an alkoxy benzene, an alkyl phenol alkyl ether, a naphthol, a hydroxy anthracene, a hydroxy 1 to 4 carbon alkyl naphthalene, a hydroxy phenylnaphthalene, a hydroxy methoxynaphthalene, a cyclohexyl phenol, or a hydroxy phenanthrene with hydrogen peroxide in a solution in substantially water-free organic solvent which solvent forms an azeotrope with water, the boiling point of the azetrope being below the boiling point of hydrogen peroxide, based on normal pressure, said reaction being carried out in the presence of sulfur dioxide as a catalyst.

2. A process according to claim 1 wherein the water content of the solvent is below 0.5%.

3. A process according to claim 2 wherein the water content of the solvent is 0.1 percent by weight.

4. A process according to claim 1 wherein the solvent is an ether or an alkyl or cycloalkyl ester of a saturated, aliphatic carboxylic acid, which ester contains a total of 4–8 carbon atoms.

5. A process according to claim 4 wherein the solvent is an alkyl or cycloalkyl ester of a saturated aliphatic carboxylic acid, which ester contains a total of 4–8 carbon atoms.

6. A process according to claim 5 wherein the solvent is an alkyl alkanoate.

7. A process according to claim 4 wherein the solvent is an ester of acetic acid or propionic acid.

8. A process according to claim 7 wherein the hydrogen peroxide is employed as a solution in n-propyl acetate or isopropyl acetate.

9. A process according to claim 8 wherein the sulfur dioxide is added as a solution in an alkyl or cycloalkyl ester of a saturated, aliphatic carboxylic acid, which ester contains a total of 4–8 carbon atoms.

10. A process according to claim 7 wherein the sulfur dioxide is added as a solution in an alkyl or cycloalkyl ester of a saturated, aliphatic carboxylic acid, which ester contains a total of 4–8 carbon atoms.

11. A process according to claim 4 wherein the sulfur dioxide is added as a solution in an alkyl or cycloalkyl ester of a saturated, aliphatic carboxylic acid, which ester contains a total of 4–8 carbon atoms.

12. A process according to claim 1 wherein the $SO_2$ is added in gaseous form.

13. A process according to claim 12 wherein there is employed sulfur dioxide in an amount of 0.0001 to 0.1 mole per mole of hydrogen peroxide.

14. A process according to claim 11 wherein there is employed sulfur dioxide in an amount of 0.0001 to 0.1 mole per mole of hydrogen peroxide.

15. A process according to claim 10 wherein there is employed sulfur dioxide in an amount of 0.0001 to 0.1 mole per mole of hydrogen peroxide.

16. A process according to claim 9 wherein there is employed sulfur dioxide in an amount of 0.0001 to 0.1 mole per mole of hydrogen peroxide.

17. A process according to claim 8 wherein there is employed sulfur dioxide in an amount of 0.0001 to 0.1 mole per mole of hydrogen peroxide.

18. A process according to claim 7 wherein there is employed sulfur dioxide in an amount of 0.0001 to 0.1 mole per mole of hydrogen peroxide.

19. A process according to claim 5 wherein there is employed sulfur dioxide in an amount of 0.0001 to 0.1 mole per mole of hydrogen peroxide.

20. A process according to claim 1 wherein there is employed sulfur dioxide in an amount of 0.0001 to 0.1 mole per mole of hydrogen peroxide.

21. A process according to claim 20 wherein there is employed 0.0005 to 0.01 mole of sulfur dioxide per mole of hydrogen peroxide.

22. A process according to claim 18 wherein the molar ratio of substituted phenol or phenol ethyl to hydrogen peroxide is from 5 to 20:1.

23. A process according to claim 1 wherein the starting compound is an alkyl phenol, an aryl phenol, a halophenol, an alkoxyphenol, a phenylalkylether, an alkyl phenol alkylether, a napthol, a hydroxyanthracene or a hydroxyphenanthrene.

24. A process according to claim 23 wherein the starting compound is 4-tert. butylphenol, p-cresol, 4-hydroxybiphenyl, anisole, 4-ethylphenol or o-cresol.

25. A process according to claim 1 wherein the starting compound is 2-chlorophenyl, 3-chlorophenol, 4-chlorophenol, 2-fluorophenol, 3-fluorophenol, 4-fluorophenol, 4-carbomethoxyphenol, 2-methylphenol, 3-methylphenol, 4-methylphenol, 4-cyclohexylphenol, 2-cyclohexylphenol, 4-phenylphenol, 3-phenylphenol, 2-phenylphenol, 4-ethylphenol, 3-ethylphenol, 2-ethylphenol, 2-isopropylphenol, 3-isopropylphenol, 4-isopropylphenol, 4-tert.-butylphenol, phenylmethylether, 4-chlorophenylmethylether, 3-chlorophenylmethylether, 2-chlorophenylmethylether, 4-methylphenylmethylether, 3-methylphenylmethylether, 4-methoxy-1-phenylbenzene, ethyl-phenylether, isopropylphenylether, isopropyl-4'-methylphenylether, 1hydroxynaphthalene, 2-hydroxynaphthalene, 1-methoxynaphthalene, 1-hydroxy-2-methylnaphthalene, 1-hydroxy-4-methylnaphthalene, 2-hydroxy-1-methylnaphthalene, 2-hydroxy-6-methylnaphthalene, 1-hydroxy-4-isopropylnaphthalene, 1-hydroxy-4tert.-butyl-naphthalene, 1-hydroxy-6-phenylnaphthalene, 1-hydroxy-6-methoxynaphthalene, isopropyl-1-naphthylether, isopropyl-2-naphthylether, phenyl-1-naphthylether, phenyl-2-naphthylether, 1-hydroxyanthracene, 1-methoxyanthracene, 2-hydroxyanthracene, 2-methoxyanthracene, 1-hydroxyphenanthrene, 3-hydroxyphenanthrene, 9-methoxyphenanthrene, 3-methoxyphenanthrene, 1-methoxyphenanthrene.

26. A process according to claim 1 wherein the starting phenol, hydroxynaphthalene, hydroxyanthracene, hydroxyphenanthrene, phenyl alkyl ether, naphthyl alkyl ether, phenanthracenyl alkyl ether or anthracenyl alkyl ester is free from substituents other than halogen, alkyl, cyclohexyl or phenyl.

27. A process according to claim 26 wherein the chain length of any alkyl group present is 1 to 4 carbon atoms and the chain length of any alkoxy group present is 1 to 2 carbon atoms.

28. A process according to claim 4 wherein the solvent is dioxane, diispropyl ether, methyl tert. butyl ether or an alkyl or cycloalkyl ester of a saturated aliphatic carboxylic acid, said ester containing 4–8 carbon atoms.

29. A process according to claim 1 wherein the temperature is 20° to 200° C.

30. A process according to claim 29 wherein the temperature is 40° to 180° C.

* * * * *